United States Patent [19]

Dardel

[11] Patent Number: 5,261,409
[45] Date of Patent: Nov. 16, 1993

[54] PUNCTURING DEVICE FOR BLOOD VESSELS

[75] Inventor: Eric Dardel, Seuzach, Switzerland

[73] Assignee: Sulzer Brothers Limited, Winterthur, Switzerland

[21] Appl. No.: 874,498

[22] Filed: Apr. 27, 1992

[30] Foreign Application Priority Data

May 27, 1991 [CH] Switzerland .................. 01561/91

[51] Int. Cl.$^5$ .............................................. A61B 8/00
[52] U.S. Cl. ................... 128/662.05; 128/662.03; 128/661.09
[58] Field of Search .............. 128/662.05, 661.09, 128/661.1, 661.07, 661.08, 662.03, 663.01

[56] References Cited

U.S. PATENT DOCUMENTS

| | | | |
|---|---|---|---|
| 4,127,842 | 11/1978 | Hassler | 128/661.09 |
| 4,501,278 | 2/1985 | Yamaguchi et al. | 128/662.05 |
| 4,867,169 | 9/1989 | Machida et al. | 128/662.03 |
| 5,052,396 | 10/1991 | Wedel et al. | 128/662.05 |
| 5,076,279 | 12/1991 | Arenson et al. | 128/662.05 |
| 5,080,104 | 1/1992 | Marks et al. | 128/662.05 |

FOREIGN PATENT DOCUMENTS

| | | | |
|---|---|---|---|
| 0396874 | 11/1990 | European Pat. Off. | 128/662.05 |
| 3329041 | 2/1984 | Fed. Rep. of Germany | 128/662.05 |
| 8403034 | 8/1984 | World Int. Prop. O. | 128/662.05 |

Primary Examiner—William E. Kamm
Assistant Examiner—George Manuel
Attorney, Agent, or Firm—Townsend and Townsend Khourie and Crew

[57] ABSTRACT

The puncturing device for blood vessels has an ultrasound probe (20) which permits location, based on the Doppler effect, of the blood vessel (50). By means of a guide duct (13) the puncturing needle (30) can be directed at least approximately coaxially relative to the beam transmitted by the probe (20). Puncturing must be performed in a sterile manner. To this end, according to the invention, the probe is enveloped in a sterile covering, this covering having a sterile coupling member (1) in which a reflector (12) for the ultrasound beam and a needle guide duct (13) are situated. The coupling member (1) may be part of the covering; alternatively, however, it may be designed as an attachment to be placed on the covering. The sterile covering with the coupling member (1), which is intended to be used once only, eliminates the need for time-consuming, repeated gas sterilization of the puncturing device.

12 Claims, 3 Drawing Sheets

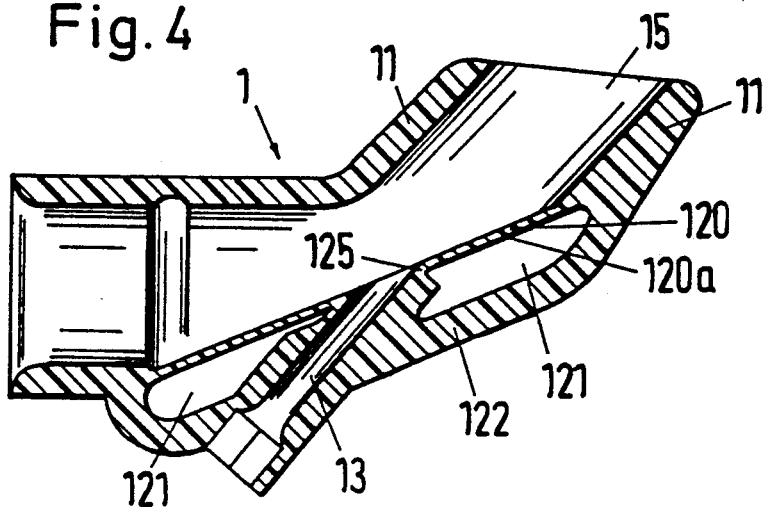
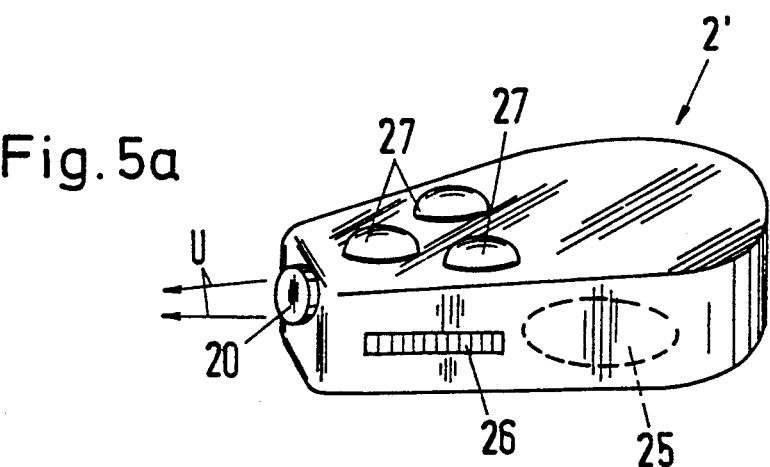
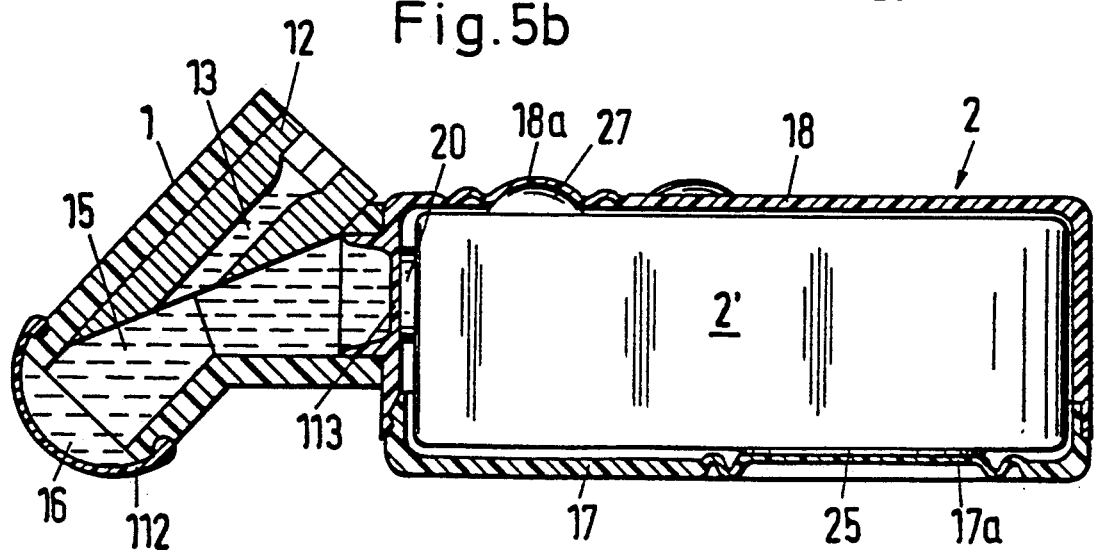

PUNCTURING DEVICE FOR BLOOD VESSELS

BACKGROUND OF THE INVENTION

The invention relates to puncturing devices for blood vessels having an ultrasound probe for Doppler-effect-based location of the blood vessel, with a guide duct for a puncturing needle, through which duct on entry into the body the needle axis can be moved at least approximately coaxially relative to the beam transmitted by the probe, and sterile coverings for such puncturing devices. The ultrasound probe in such a device has a transmitter/receiver system by means of which ultrasound can be irradiated into the body and a signal from the partly reflected beam can be recorded. Due to the Doppler effect, reflection by the flowing blood leads to a frequency shift from which an acoustic and/or optical signal can be obtained. By seeking a maximum for such a signal it is possible to find the point of penetration for the puncturing needle.

Devices of this type are known, for example, from Swiss patent specification 676 787 (=P. 6297). The transmitter/receiver system is so constructed that a guide duct for the needle runs through the acoustic resonator. This design is disadvantageous because puncturing must be performed under sterile conditions and because the required gas sterilization of the ultrasound probe is very time-consuming. In a simpler ultrasound probe without an integrated guide duct sterility can be achieved with a sterile covering intended for use once only (see for example EP-A 0 104 618). In these simpler probes, however, the needles cannot run coaxial with the ultrasound beam transmitted.

SUMMARY OF THE INVENTION

An object of the invention is to create a puncturing device, the ultrasound probe of which can be enveloped in a sterile covering, and the needle can be guided at least approximately coaxially relative to the beam transmitted. This object is achieved in that between the probe and the surface of the body a sterile coupling member is provided which deflects the ultrasound beam, comprises the needle guide duct and is part of or an attachment for a covering by means of which the probe can be enclosed at least in part in a sterile manner. A coupling member, which directs the ultrasound via reflection by a reflector surface into the body, and in which the needle guide duct is provided, is made from sterile or sterilizable material. This coupling member may be part of the sterile covering; alternatively, however, it may be an attachment which can be placed on the covering. The sterile covering with the coupling member is preferably intended for only one use.

In a compact puncturing device which can be held in the hand, the covering is formed in such a way that the device is entirely enclosed. In other puncturing devices, in which for example the optical and/or acoustic indicator means are housed in a stationary device portion set up separately, it is sufficient if only the puncturing device in the treatment area (that is, the probe and possibly part of the connecting lead) is in a sterile envelope.

The coupling member may be made from a solid material which conducts ultrasound well, the ultrasound reflector being formed for example by a free external surface disposed in accordance with sonic optics. The coupling member may alternatively comprise a housing filled with a gel which conducts ultrasound satisfactorily, the reflector consisting for example of a metal member which at the same time forms part of the housing wall and the needle guide duct.

BRIEF DESCRIPTION OF THE DRAWINGS

FIG. 4 illustrates the coupling member in a third embodiment, with an ultrasound reflector in the form of a synthetic plastics diaphragm instead of a metal member;

FIG. 5a illustrates a non-sterile part of a compact puncturing device;

FIG. 5b represents a longitudinal section through a covering embodying the invention for the device part shown in FIG. 5a (fourth embodiment);

DESCRIPTION OF PREFERRED EMBODIMENTS

Figure 1:
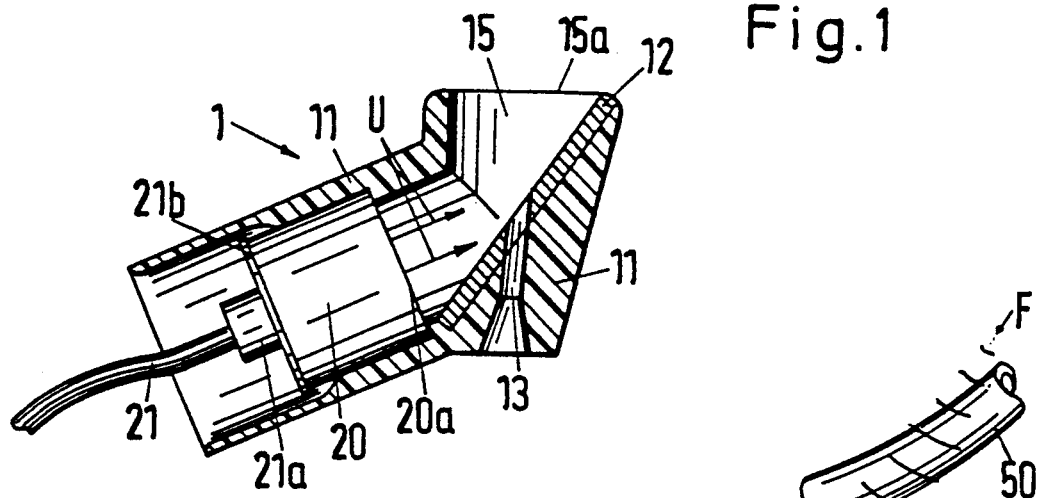
FIG. 1 illustrates a first embodiment of an ultrasound probe with a sterile covering in accordance with the invention.

In the first embodiment (FIG. 1) the following parts are visible: the coupling member 1 with the housing 11, which may, for example, be injection-moulded from synthetic plastic material, the ultrasound reflector 12 (reflector for the ultrasound beam), which consists of a flat metal plate, and the needle guide duct 13 which traverses the central area of the reflector; in addition the ultrasound probe 20 which is connected by a cable 21 to a stationary portion (not shown) of the puncturing device.

The ultrasound probe 20 emits an ultrasound beam (symbolised by two arrows U) into a cavity 15 filled with a coupling gel (not shown), the beam being reflected off the reflector 12 to the outlet aperture 15a. The outlet aperture 15a in this first embodiment is circular, and the ultrasound beam comes out perpendicular to this aperture. The needle guide duct 13, accordingly, is also perpendicular to the outlet aperture 15a. When the puncturing device is in use the aperture 15a is held at an angle to the surface of the body, and the wedge-shaped gap is filled with coupling gel.

The probe 20 can be pushed into the housing 11. Advantageously, the probe 20 is so designed that the connecting cable 21 can be attached to the probe head with a plug 21a and cover plate 21b. This connecting cable 21 and the coupling member 1 are packed in a sterile state, and only immediately before treatment are they unpacked and connected to the ultrasound probe 20 to form a sterile puncturing device ready for use. Precautions, for example, the use of sterile tongs, must of course be taken to ensure that the non-sterile probe 20 does not contaminate the outer surfaces of the coupling member 1 and cover plate 21b which form the sterile probe covering.

When the probe 20 is pushed into the housing 11, an air bubble may be trapped between the end face 20a of the probe and the coupling gel in the cavity 15. Advantageously, therefore, a ventilation duct is provided, for example a bore or groove in the housing wall (not shown).

Figure 2:
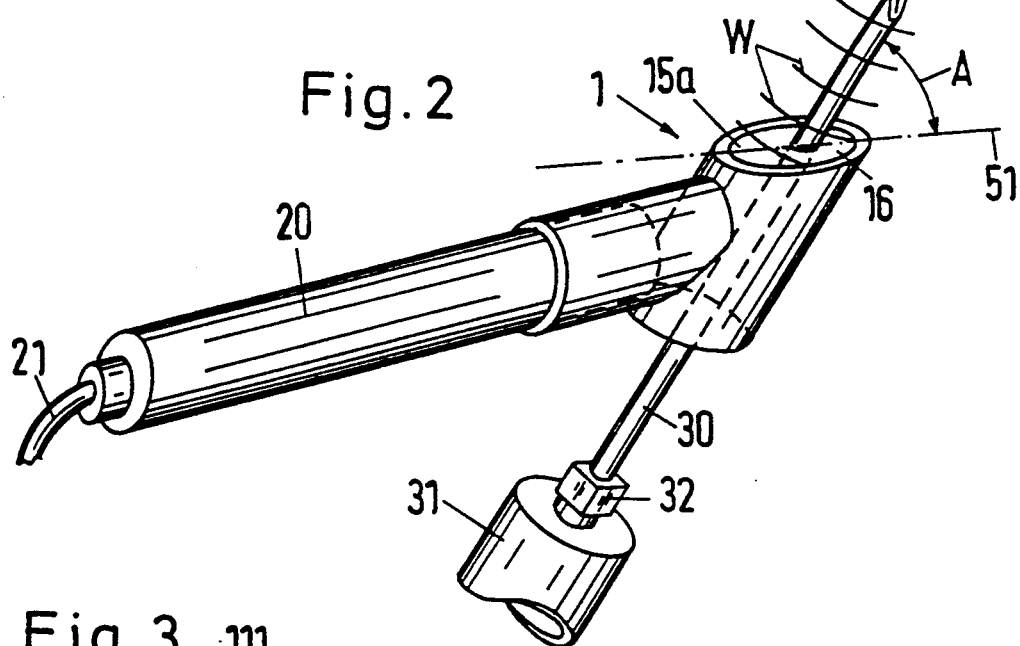
FIG. 2 is a perspective view of a second embodiment.

In the second embodiment (FIGS. 2 and 3) the ultrasound probe 20 is rod-shaped, and the coupling member 1 directs the ultrasound waves (symbolised by arcs W) at an acute angle A through the elliptical outlet aperture 15a. In this case the outlet aperture 15a can be laid flat on the surface of the body (indicated by a chain line 51). The needle 30, which is attached to a syringe 31, is driven along the convergent ultrasound beam (focus F)—after location of the blood vessel 50 by means of the Doppler effect-into this vessel 50. In FIG. 2 the coupling gel 16 is indicated, with which the cavity 15 (FIG. 3) is filled.

The ultrasound reflector 12 in the second embodiment is formed by an obliquely cut circular cylinder, for example of steel. The longitudinal bore 13 acting as the needle guide may run centrally or be slightly off-centre. At the mouth 14 of the duct 13 the duct cross-section is expanded so that it fits positively, for example, on a square member 32, which is provided at the rear end of the needle 30 for the following purpose. After puncturing of the blood vessel 50 the syringe 31 must be removed from the needle 30. To this end the probe 20 with the coupling member 21 is pushed back along the gripped needle 30, so introducing the square member 14 into the duct mouth 32. While the probe 20 continues to be held with one hand, the syringe 31 can be removed from the needle with the other hand; turning of the needle 30 is meanwhile prevented by the square member 32. Instead of the square member 32 and the corresponding duct mouth 14, of course, other means could be used to prevent turning of the needle 30.

Figure 3:
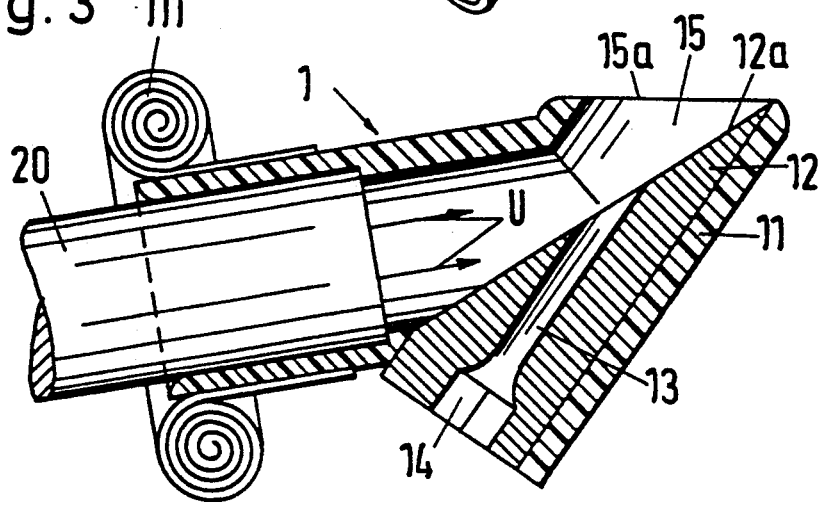
FIG. 3 represents a longitudinal section through the coupling member of the second embodiment.

Immediately before puncturing the sterile coupling member 1 is attached to the rod-like ultrasound probe, the probe area not covered by the coupling member being first enveloped for example in a sterile covering or a sterile latex hose. It is also possible to mount a rolled-up hose 111 of elastomeric material on the coupling member 1 as shown in FIG. 3. This coupling member 1 is attached to the non-sterile probe, whereupon the hose 111 can be unrolled onto the probe. The hose 111 can also be used to envelop part of the connecting cable 21, in which case the latter does not need to be sterile.

The ultrasound reflector 12 may be made from an impervious material, for example metal or glass. There are however also other possibilities: FIG. 4 illustrates an embodiment in which the ultrasound reflector is formed by a diaphragm 120 spanning a cavity 121. The ultrasound, which is propagated in the gel-filled cavity 15 and in the diaphragm 120, is reflected at the interface 120a between the diaphragm 120 and cavity 121. The wall portion 122 forms the frame over which the diaphragm 120 is stretched. Where the needle guide duct 13 passes through the diaphragm 120, no ultrasound is reflected. Advantageously, therefore, the duct wall 125 is thin in the vicinity of the diaphragm 120.

The fourth embodiment (FIGS. 5a and 5b) is a compact puncturing device 2 which is battery-operated and has both acoustic and optical indicator means, for example a loudspeaker 25 and a chain of light-emitting diodes 26, by means of which the signals arising from the Doppler effect can be indicated. The device also has operating buttons 27, by means of which the device can be switched on and off and, for example, the volume can be regulated. The puncturing device 2 comprises on the one hand the non-sterile device portion 2' with the ultrasound probe 20, indicator means 25, 26 and operating buttons 27, and on the other hand the sterile covering in accordance with the invention, composed of a lower shell member 17 and upper shell member 18 with the coupling member 1. The covering is so designed that between the loudspeaker 25 and the wall 17a of the covering there is a satisfactory sound-radiating connection, and the covering wall 18a beside the operating buttons 27 is flexible, so that the buttons can be pushed. The covering must be made from transparent material so that the optical indication 27 is visible.

The coupling member 1 in the fourth embodiment is of a similar design to that in the second embodiment (FIG. 3); obviously, other designs are also possible here. FIG. 5b illustrates further features of the coupling member 1, which may also be used in the other embodiments: the coupling member 1 is sealed on the body side with a diaphragm 112 of elastomeric material, and the coupling gel 16 is separated from the probe 20 by a diaphragm 113. Because of the convex shape of the flexible diaphragm 112, the coupling member 1 can mold itself to the surface of the body to which it is applied. During operation the diaphragm 112 is penetrated with the needle. The needle guide duct 13 may also be closed with a penetrable diaphragm (not shown), to prevent gel 16 from escaping from the cavity 15. The diaphragm 113, which may be very thin, must rest closely on the radiation surface of the ultrasound probe 20, to minimize losses in sound transmission at this interface.

Figure 6A:
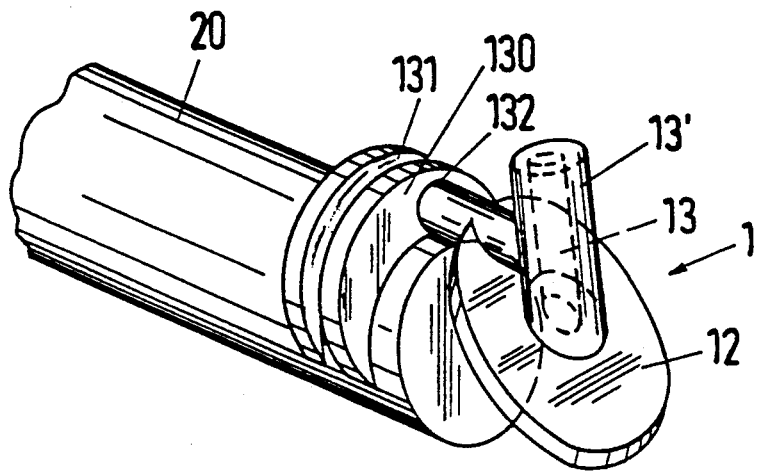
FIG. 6a illustrates a probe head with a detachable coupling member.
Figure 6B:
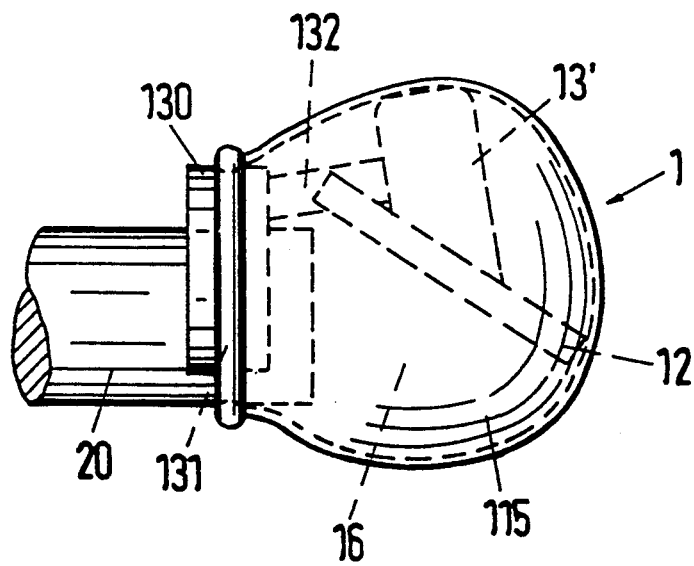
FIG. 6b shows the coupling member from FIG. 6a with a gel-filled "balloon".

The coupling member 1 in the fourth embodiment may be regarded as an attachment to the sterile covering formed by the two shell members 17, 18. FIG. 6a illustrates another example of a coupling member 1 in the form of an attachment. This coupling member 1 is attached to a probe 20 which has first been enveloped in a sterile, bag-like hose of elastomeric material. The coupling member 1 comprises the reflector 12, the needle guide 13' (with the needle guide duct 13), the clip 130, which for example comprises a groove 131, and the connecting member 132. The gap between the probe 20, reflector 12 and body surface must of course be filled again with coupling gel 16. A gel-filled "balloon" 115 enveloping the coupling member 1 as shown in FIG. 6b fulfils this requirement in a practical manner.

I claim:

1. A puncturing device for blood vessels comprising:
   an ultrasound probe having means for emitting an ultrasound beam;
   a guide duct adapted to receive a puncturing needle, the puncturing needle having a needle axis when positioned in the guide duct; and
   a sterile coupling member coupled to the probe and having a means for deflecting the ultrasound beam emitted by the probe, the deflecting means for deflecting the ultrasound beam emitted by the probe in a direction substantially coaxial to the needle axis when the puncturing needle is positioned in the guide duct.

2. The puncturing device as claimed in claim 1, wherein the coupling member comprises a housing including a wall with reflector means, the housing further comprising a coupling gel filling the housing, and the needle guide duct being disposed axially within the housing.

3. The puncturing device as claimed in claim 2, wherein the coupling member further comprises a diaphragm made of an elastomeric material connected to the housing and adapted to be positioned against a body.

4. The puncturing device as claimed in claim 2, further comprising a diaphragm positioned between the coupling gel and the probe.

5. The puncturing device as claimed in claim 2, wherein the reflector means comprises a material selected from a group consisting of metal and glass.

6. The puncturing device as claimed in claim 1, wherein the coupling member is attached to the probe at a point of connection, the coupling member comprising a rolled-up hose positioned near the point of connection, being made of an elastomeric material, and sized so that the rolled-up hose can be unrolled over the probe.

7. The puncturing device as claimed in claim 1, comprising battery means for operating the puncturing device in a battery-operated mode, and comprising indicating means for coupling said battery means operably to the probe, operating buttons, and a covering being at least partially sound-transmitting, transparent and flexible.

8. The puncturing device as claimed in claim 1, further comprising a sterile cover for enveloping at least partially the probe.

9. The puncturing device as claimed in claim 1, wherein the deflecting means comprises a reflector, and the coupling member further comprises a needle guide and a coupling gel, the reflector, the needle guide and the coupling gel being enclosed in a balloon-like diaphragm.

10. The puncturing device as claimed in claim 1, further comprising means for precluding rotation of the puncturing needle within the guide duct about the needle axis when the puncturing needle is positioned in the guide duct.

11. The puncturing device as claimed in claim 1, further comprising a sterile covering which covers at least a part of the device.

12. A puncturing device for blood vessels comprising:
   an ultrasound probe having means for emitting an ultrasound beam;
   a guide duct adapted to receive a puncturing needle, the puncturing needle having a needle axis when positioned in the guide duct;
   a sterile coupling member coupled to the probe and having a reflector, the reflector being configured and positioned to receive and reflect the ultrasound beam emitted by the probe in a direction substantially coaxial to the needle axis when the puncturing needle is positioned in the guide duct, the sterile coupling member further comprising a housing including a wall having the reflector, the housing further comprising a coupling gel filling the housing, and the needle guide duct being disposed in a central area of the reflector; and
   a diaphragm positioned between the needle guide duct and the coupling gel.

* * * * *